(12) United States Patent
Mullenix et al.

(10) Patent No.: US 10,197,583 B2
(45) Date of Patent: Feb. 5, 2019

(54) HYDROXYCHOLESTEROL IMMUNOASSAY

(71) Applicant: ENZO LIFE SCIENCES, INC. C/O ENZO BIOCHEM, INC., New York, NY (US)

(72) Inventors: Michael C. Mullenix, Saline, MI (US); Robert Elliot Zipkin, Wynnewood, PA (US); Jeffrey Kroll Adams, Fort Washington, PA (US); Wayne Forrest Patton, Dix Hills, NY (US); James J. Donegan, Long Beach, NY (US)

(73) Assignee: Enzo Life Sciences, Inc., Farmingdale, NY (US)

(*) Notice: Subject to any disclaimer, the term of this patent is extended or adjusted under 35 U.S.C. 154(b) by 189 days.

(21) Appl. No.: 15/484,754

(22) Filed: Apr. 11, 2017

(65) Prior Publication Data

US 2017/0219612 A1   Aug. 3, 2017

Related U.S. Application Data

(60) Continuation of application No. 14/572,061, filed on Dec. 16, 2014, now abandoned, which is a division of application No. 12/927,206, filed on Nov. 9, 2010, now Pat. No. 8,969,525.

(51) Int. Cl.
| | |
|---|---|
| *G01N 33/92* | (2006.01) |
| *C07J 43/00* | (2006.01) |
| *C07J 9/00* | (2006.01) |
| *C07K 16/44* | (2006.01) |
| *G01N 33/569* | (2006.01) |
| *G01N 33/53* | (2006.01) |
| *C07K 16/18* | (2006.01) |

(52) U.S. Cl.
CPC .......... *G01N 33/92* (2013.01); *C07J 9/00* (2013.01); *C07J 43/003* (2013.01); *C07K 16/18* (2013.01); *C07K 16/44* (2013.01); *G01N 33/5308* (2013.01); *G01N 33/56966* (2013.01); *C07K 2317/21* (2013.01); *G01N 2800/285* (2013.01); *G01N 2800/2835* (2013.01); *G01N 2800/52* (2013.01)

(58) Field of Classification Search
CPC .......... C07J 43/003; C07J 9/00; C07K 16/18; C07K 16/44; C07K 2317/21; G01N 2800/2835; G01N 2800/285; G01N 2800/52; G01N 33/5308; G01N 33/56966; G01N 33/92
See application file for complete search history.

(56) References Cited

U.S. PATENT DOCUMENTS

| | | |
|---|---|---|
| 4,081,525 A | 3/1978 | Knight |
| 4,585,862 A | 4/1986 | Wang et al. |
| 8,969,525 B2 | 3/2015 | Mullenix |
| 2008/0177059 A1 | 7/2008 | Bitman et al. |
| 2012/0052481 A1 | 3/2012 | Rabbani et al. |
| 2015/0104817 A1 | 4/2015 | Mullenix |
| 2015/0140004 A1 | 5/2015 | Mullenix |

FOREIGN PATENT DOCUMENTS

| | | |
|---|---|---|
| DE | 2429644 | 1/1975 |
| JP | 57112400 | 7/1982 |

(Continued)

OTHER PUBLICATIONS

Alexandrov et al., 24S-hydroxycholesterol induces infammatory gene expression in primary human neural cells, NeuroReport 2005:909-913, 16.

Magnus Axelson, Occurrence of isomeric dehydrocholesterols in human plasma, J. Lipid Res. 1991,1441-1448, 32.

Biro et al., Novel anti-cholesterol monoclonal immunoglobulin G antibodies as probes and potential modulators of membrane raft-dependent immune functions, J. Lipid Res. 2007,19-29, 48.

Bjorkhem, et al.,Oxysterols and neurodegenerative diseases, Molecular Aspects of Medicine, 2009, 171-179, 30.

Blomberg et al., Terbium and Rhodamine as Labels in a Homogeneous Time-resolved Fluorometric Energy Transfer Assay of the b Subunit of Human Chorionic Gonadotropin in Serum, Clinical Chemistry 1999, 855-861, 45:6.

Breitillon et al., Plasma levels 24S-hydroxycholesterol reflect the balance between cerebral production and hepatic metabolism and are inversely related to body surface, J. Lipid Res. 2000, 840-845, 41.

(Continued)

*Primary Examiner* — Galina Yakovleva
(74) *Attorney, Agent, or Firm* — Paul Diamond, Esq.

(57) ABSTRACT

Provided is a derivative of 22-hydroxycholesterol, 24S-hydroxycholesterol, 25-hydroxycholesterol, 26-hydroxycholesterol or 27-hydroxycholesterol. Also provided is a protein conjugated to the above derivative. Further provided is an antibody composition comprising antibodies that specifically bind to 22-hydroxycholesterol, 24S-hydroxycholesterol, 25-hydroxycholesterol, 26-hydroxycholesterol or 27-hydroxycholesterol. Additionally, a method of making antibodies that specifically bind to 22-hydroxycholesterol, 24S-hydroxycholesterol, 25-hydroxycholesterol, 26-hydroxycholesterol or 27-hydroxycholesterol is provided. Also, a method of assaying for 22-hydroxycholesterol, 24S-hydroxycholesterol, 25-hydroxycholesterol, 26-hydroxycholesterol or 27-hydroxycholesterol is provided. Additionally provided is a kit for detecting 22-hydroxycholesterol, 24S-hydroxycholesterol, 25-hydroxycholesterol, 26-hydroxycholesterol or 27-hydroxycholesterol. A method of detecting an enzyme or enzymes utilized in phase II drug metabolism is also provided. Also, a method of detecting an enzyme that synthesizes 22-hydroxycholesterol, 24S-hydroxycholesterol, 25-hydroxycholesterol, 26-hydroxycholesterol or 27-hydroxycholesterol is provided. Further provided is a method of evaluating progression of multiple sclerosis in a patient. Also provided is a method of determining whether a treatment for multiple sclerosis in a patient is effective. Further, a method of evaluating progression of Huntington's disease in a patient is provided. Additionally provided is a method of determining whether a treatment for Huntington's disease in a patient is effective.

2 Claims, 1 Drawing Sheet

(56) References Cited

FOREIGN PATENT DOCUMENTS

| JP | 5194584 | 8/1993 |
|---|---|---|
| JP | 2003012692 | 1/2003 |

OTHER PUBLICATIONS

Bryleva et al., ACAT1 gene ablation increases 24(S)-hydroxycholesterol content in the brain and ameliorates amyloid pathology in mice with AD, PNAS, Feb. 16, 2010, 3081-3086, 107.

Burkard et al., Determination of 24S- and 27-hydroxycholesterol in plasma by high-performance liquid chromatography-mass spectrometry, J. Lipid Res. 2004, 776-781, 45.

Charlton and Porter, Isolation of Anti-Hapten Specific Antibody Fragments from Combinatorial Libraries, Methods in Molecular Biology, Antibody Phage Display: Methods and Protocols, 2002, 159-171, 178.

Cook et al., 24-Hydroxycholesterol Sulfation by Human Cytosolic Sulfotransferases: Formation of Monosulfates and Disulfates, Molecular Modeling, Sulfatase Sensitivity, and Inhibition of Liver X Receptor Activation, 2009, Drug Metab. Dispos. 2069-2078, 37.

Coughtrie et al., A General Assay for UDPglucuronosyltransferase Activity Using Polar Amino-Cyano Stationary Phase HPLC and UDP[U-14C]Glucuronic Acid, Analytical Biochemistry 1986, 198-205, 159.

Debarber et al., Liquid chromatography-tandem mass spectrometry determination of plasma 24S-hydroxycholesterol with chromatographic separation of 25-hydroxycholesterol, Analytical Biochemistry 2008, 151-153, 381.

Dijkstra et al., Interaction of Anti-Cholesterol Antibodies with Human Lipoproteins, The Journal of Immunology, 1996, 2006-2013, 157.

Garcia et al., Cyp46 Polymorphisms in Alzheimer's Disease: A Review, J Mol Neurosci 2009, 342-345, 39.

Hudry et al. Adeno-associated Virus Gene Therapy With Cholesterol 24-Hydroxylase Reduces the Amyloid Pathology Before or After the Onset of Amyloid Plaques in Mouse Models of Alzheimer's Disease, Molecular Therapy 2010, 44-53,18.

Michael Irizarry, Biomarkers of Alzheimer Disease in Plasma, NeuroRx,2004, 226-234, 1.

Jennings et al., Cholesterol inhibits spontaneous action potentials and calcium currents in guinea pig gallbladder smooth muscle, Am. J. Physiol. (Gastrointest. Liver Physiol. 40) 1999, G1017-G1026, 277.

Kolsch et al., Altered levels of plasma 24S- and 27-hydroxycholesterol in demented patients, Neuroscience Letters 2004, 303-308, 368.

Koschack et al., Serum 24S-hydroxycholesterol and hippocampal size in middle-aged normal individuals, Neurobiology of Aging, 2009, 898-902, 30.

Leoni et al., Links between ApoE, brain cholesterol metabolism, tau and amyloid β-peptide in patients with cognitive impairment, Biochem. Soc. Trans. 2010, 1021-1025, 38.

Leoni et al., Plasma 24S-hydroxycholesterol and caudate MRI in pre-manifest and early Huntington's disease, Brain 2008, 2851-2859, 131.

Leoni et al., Changes in human plasma levels of the brain specific oxysterol 24S-hydroxycholesterol during progression of multiple sclerosis, Neuroscience Letters, 2002, 163-166, 31.

Valerio Leoni, Oxysterols as markers of neurological disease—a review, The Scandinavian Journal of Clinical & Laboratory Investigation, 2009, 22-25, 69.

Lutjohann et al., Plasma 24S-hydroxycholesterol (cerebrosterol) is increased in Alzheimer and vascular demented patients, J. Lipid Res. 2000, 195-198, 41.

Lutjohann and Von Bergmann, 24S-hydroxycholesterol: a marker of brain cholesterol metabolism, Pharmacopsychiatry, 2003, s102-s106, 36 Supp.

Lutjohann et al., Cholesterol homeostasis in human brain: Evidence for an age-dependent flux of 24S-hydroxycholesterol from the brain into the circulation, Proc. Natl. Acad. Sci. USA 1996, 9799-9804, 93.

Mayilo et al., Competitive homogeneous digoxigenin immunoassay based on fluorescence quenched by gold nanoparticles, Analytica Chimica Acta, 2009, 119-122, 646.

MacIntosh et al., Fluorescent sterols for the study of cholesterol trafficking in living cells, Probes and Tags to Study Biomolecular Function, Lawrence Miller(Ed.), 2008, 1-20, Wiley-VCH Berlag GmbH & Co.

O'Beirne and Cooper, Heterogeneous enzyme immunoassay, J Histochem Cytochem 1979, 1148-1162, 27.

Pappassotiropoulos et al., 24S-hydroxycholesterol in cerebrospinal fluid is elevated in early stages of dementia, Journal of Psychiatric Research, 2002, 27-32, 36.

Pierce Protein Research Products, Antibody Production (Immunogen Preparation), piercenet.com/browse.cfm?fldID=4E018AA6-5056-8A76-4E57-3BC84C88A328, 2011, IP.

Sato et al., Antibody like activities against cholesterol ester in anti-ldl antiserum an observation on the surface of ldl, Biomedicine, 1976, 385-389, 24.

Shaafati et al., Levels of ApoE in cerebrospinal fluid are correlated with Tau and 24S-hydroxycholesterol in patients with cognitive disorders, Neuroscience Letters, 2007, 78-82, 425.

Solomon et al., Plasma levels of 24S-hydroxycholesterol reflect brain volumes in patients without objective cognitive impairment but not in those with Alzheimer's disease, Neuroscience Letters, 2009, 89-93, 462.

Sparrow et al., A fluorescent cholesterol analog traces cholesterol absorption in hamsters and is esterified in vivo and in vitro, J. Lipid Res. 1999, 1747-1757, 40.

Teunissen et al., Biological markers in CSF and blood for axonal degeneration in multiple sclerosis, Lancet Neurol 2005, 32-41, 4.

Teunissen et al., Decreased levels of the brain specific 24S-hydroxycholesterol and cholesterol precursors in serum of multiple sclerosis patients, Neuroscience Letters, 2003, 159-162, 347.

Valenza et al., Cholesterol biosynthesis pathway is disturbed in YAC128 mice and is modulated by huntingtin mutation, Human Molecular Genetics, 2007, 2187-2198, 16.

Vega and Weiner, Plasma 24S Hydroxycholesterol Response to Statins in Alzheimer's Disease Patients: Effects of Gender, CYP46, and ApoE Polymorphisms, J Mol Neurosci 2007, 51-55, 33.

Winter et al., Making antibodies by phage display technology, Annu Rev. Immunol. 1994, 433-455, 12.

Wong et al., Reproducibility and Correlations of Multiplex Cytokine Levels in Asymptomatic Persons, Cancer Epidemiol Biomarkers Prev 2008, 3450-3456, 17.

Yinsong et al., Preparation and characterization of self-aggregated nanoparticles of cholsterol-modified o-carboxymethyl chitosan conjugates, Carbohydrate Polymers, 2007, 597-606, 69.

Zhao et al., Polar metabolite of cholesterol induces rat cognitive dysfunctions, Neuroscience, 2009, 398-403, 164.

Frank et al., "Clinical biomarkers in drug discovery and development," *Nature Reviews Drug Discovery*, vol. 2, pp. 566-580 (2003).

Gomez-Mancilla et al., "Central Nervous System Drug Development: An Integrative Biomarker Approach Toward Individualized Medicine," *NeuroRx*, vol. 2, No. 4, pp. 683-695 (2005).

Goodrow et al., "Strategies for Immunoassay Hapten Design," *Immunoanalysis of Agrochemicals*, Nelson, J., ACS Symposium Series, vol. 586, Chapter 9, pp. 119-139 (1995).

Knerr et al., "Efficient synthesis of hydrophilic phosphodiester derivatives of lipophilic alcohols via the glycosyl hydrogenphosphonate method," *Tetrahedron Letters*, vol. 39, pp. 273-274 (1998).

Kobayashi et al., "Production and characterization of monoclonal antibodies against two haptenic derivatives of 1 appha,25-dihydroyxvitamin D3 conjugated with bovine serum albumin through the C-3 or C-24 position," *Biol. Pharm. Bull.*, vol. 20, No. 9, pp. 948-953 (1997).

Peter et al., "Synthesis von galactose-cluster-haltigen steroidderivaten. (Synthesis of galactose-cluster-containing steroid derivatives)," *Liebigs Annalen Der Chemic*, Verlag Chemie GmbH, Weinhiem, DE, vol. 9, pp. 863-869 (1990).

(56) References Cited

OTHER PUBLICATIONS

Sato et al., "Preparation of anti-etiocholenic acid antiserum and anti-cholesterol succinate antiserum and their cross reactivties," *Jpn. J. Exp. Med.*, vol. 46, No. 4, pp. 213-221 (1976).

Spencer et al., "Pharmacore analysis of the nuclear oxysterol receptor LXR alpha," *Journal of Medicinal Chemistry*, American Chemical Society. vol. 44, pp. 886-897 (2001).

Szurdoki et al., "Important Factors in Hapten Design and Enzyme-Linked Immunosorbent Assay Development," *Immunoanalysis of Agrochemicals*, Nelson, J., ACS Symposium Series, vol. 586, Chapter 4, pp. 39-63 (1995).

Thermo Scientific Pierce F(ab')2 Preparation Kits, retrieved from http://www.piercenet.com/browse.cfm?fldID=01010503 on May 31, 2012.

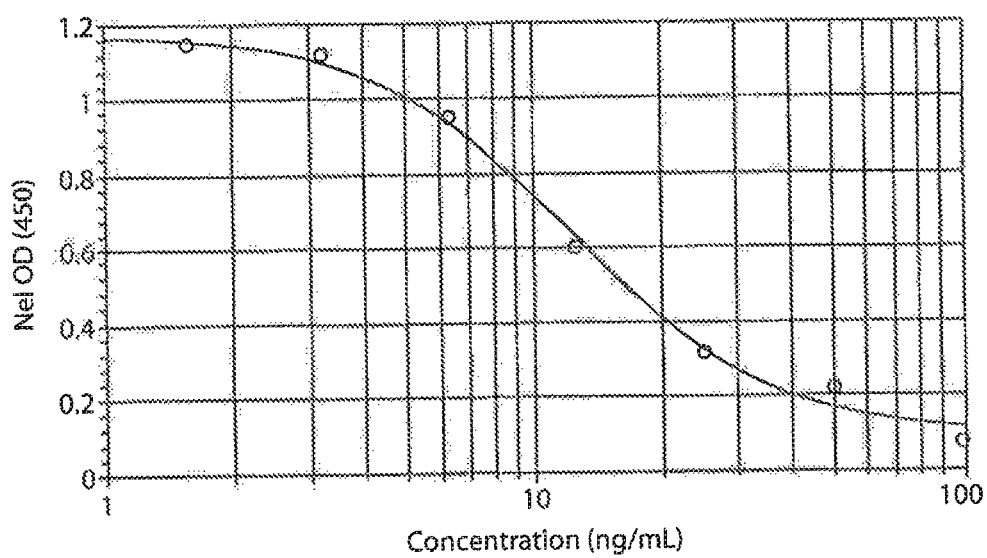

HYDROXYCHOLESTEROL IMMUNOASSAY

CROSS-REFERENCE TO RELATED APPLICATION

This application is a continuation of U.S. patent application Ser. No. 14/572,061, filed Dec. 16, 2014, which is a divisional of U.S. patent application Ser. No. 12/927,206, filed Nov. 9, 2010, which are hereby incorporated by reference in their entirety.

BACKGROUND OF THE INVENTION (1) Field of the Invention

The present application generally relates to antibody detection of metabolites. More specifically, methods and compositions are provided for preparing and using antibodies to detect and quantify 24S-hydroxycholesterol.

(2) Description of the Related Art 24S-hydroxycholesterol (24HC) (structure below) is one of several mono-oxygenated metabolites of cholesterol.

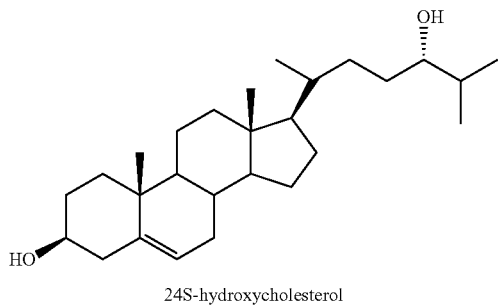 [SMILES: CC(CC[C@H](O)C(C)C)[C@H]1CCC2C3CC=C4C[C@@H](O)CC[C@]4(C)C3CC[C@@]21C]

24S-hydroxycholesterol

Excess cholesterol in the brain is converted to 24HC by cholesterol 24-hydroxylase (CYP46). Owing to its ability to cross the blood-brain barrier, 24HC is present in peripheral circulation. Because CYP46 is predominantly expressed in the brain, 24HC in plasma originates almost exclusively from the brain (Lütjohann et al., 1996). Interestingly, certain CYP46 single nucleotide polymorphisms are associated with Alzheimer's disease ("AD")(Garcia et al., 2009). Plasma levels of 24HC correlate with brain and hippocampal size (Bretillon et al., 2000; Koschack et al., 2009). 24HC in plasma or cerebrospinal fluid is an indicator of brain cholesterol turnover, particularly from myelin, and demyelination caused by neuronal degeneration results in an increased flux of 24HC across the blood-brain barrier and into plasma. Thus, active neuronal cells are the major source of 24HC in human circulation and the concentration of 24HC in plasma is considered a surrogate marker for brain cholesterol homeostasis. Additionally, 24HC is a signaling molecule in the brain, inducing ApoE-mediated cholesterol efflux from astrocytes by a direct effect on ApoE transcription, protein synthesis and secretion (Leoni et al., 2010). Direct toxic and inflammatory gene expression-inducing effects of 24HC may also be involved in the pathology of AD or other cognitive dysfunctions (Alexandrov et al., 2005; Kölsch et al., 2004; Zhao et al., 2009). Further, neurodegeneration and the resulting loss of neurons has been found in some studies to result in the reduction of 24HC in plasma in AD, Huntington's disease, and multiple sclerosis (Björkhem et al., 2009; Irizarry, 2004; Leoni, 2009; Leoni et al., 2008; Masterman et al., 2002; Solomon et al., 2009; Teunissen et al., 2003, 2005; Valenza et al., 2007). However, other studies have found increased 24HC plasma levels in AD patients (Lütjohann and von Bergmann, 2003; Lütjohann et al., 2000). In cerebrospinal fluid, 24S-hydroxycholesterol levels increase, and appear to reflect the rate of neurodegeneration (Leoni et al., 2010; Papassotiropoulos et al., 2002; Shafaati et al., 2007). Reduced plasma levels of 24HC are also induced by statin treatment (Lütjohann and von Bergmann, 2003; Vega and Weiner, 2007). In a further association with neurodegenerative disease, gene therapy with CYP46 in a mouse model of AD, administered before the onset of amyloid deposits, reduced Aβ peptides, amyloid deposits and trimeric oligomers, and improved spatial memory in those mice (Hudry et al., 2010). Additionally, ablation of acyl-CoA:cholesterol acetyltransferase 1 (ACAT1) in the brain leads to a reduction of AD-associated forms of amyloid precursor protein and increases in brain 24HC (Bryleva et al., 2010).

There is a close relationship between the biotransformation of drugs and normal biochemical processes occurring in the human body. The metabolism of drugs involves many pathways associated with the synthesis of endogenous substrates such as steroid hormones, cholesterol and bile acids. It should be recognized that many of the enzymes involved in drug metabolism are principally designed for the metabolism of these endogenous compounds. These enzymes metabolize drugs only because the drugs resemble the natural substrate.

During phase II metabolism, a substrate is rendered more hydrophilic through the covalent attachment of an endogenous molecule. The cytosolic sulfotransferase (SULT) and UDP-glucuronosyltransferase (UGT) families of enzymes account for the majority of phase II metabolism in humans and animals. Sulfonation and glucuronidation are generally considered competing pathways. Typically, sulfonation predominates at low substrate concentrations, while glucuronidation predominates at higher concentrations.

In both brain and liver, 24HC serves as a liver-X receptor (LXR) agonist and has an important role in cholesterol homeostasis. Conversion of this metabolite to bile acids accounts for only 40-50% of the metabolite's elimination, leaving a large percentage of 24HC metabolism and excretion occurring by other pathways. The SULT and UGT enzymes represent a highly responsive defense system against the mutagenicity of carcinogenic environmental chemicals and the toxicity of xenobiotics and endogenous metabolic intermediates. Conjugation with either sulfonate or glucuronic acid has been implicated as important for biliary excretion of 24HC.

Cytosolic SULTs are involved with the conjugation of therapeutic drugs, xenobiotics and small endogenous compounds including hydroxysteroids, thyroid hormones, estrogens, bile acids, cholesterol and oxysterols. 24HC can be conjugated by at least three isoforms of human cytosolic SULTs, but others (e.g. SULTs 1A1, 1A3, 1B1, 1C1) display no discernable activity (Cook et al., 2009). SULTs 2A1 and 1E1 sulfonate both the 3- and 24-hydroxyl groups to form 24-hydroxycholesterol-3,24-disulfate. SULT2B1b forms only 24-hydroxycholesterol-3-sulfate. The 3-sulfate as a monosulfate or as the disulfate can be hydrolyzed by human placental steroid sulfatase, whereas the 24-sulfate is resistant to its actions. Both the 24-hydroxycholesterol-3-sulfate and 24-sulfate are antagonists of LXR activation.

Current methods for determination of 24HC generally involve gas chromatography-mass spectrometry, or liquid chromatography-tandem mass spectrometry (see, e.g., Berkard et al., 2004; DeBarber et al., 2008; Leoni et al., 2008). Because the importance of 24HC in human physiology and disease is being increasingly recognized, and because the current methods for identifying 24HC are time consuming and require expensive equipment, there is a need for a simpler assay for 24HC. The present invention addresses that need.

BRIEF SUMMARY OF THE INVENTION

The inventors have developed methods for preparing antibodies to 24S-hydroxycholesterol (24HC). The prepared antibodies have low cross-reactivity to related metabolites, and are useful reagents for specific and sensitive immunoassays for 24HC.

Thus, in some embodiments, a derivative of 22-hydroxycholesterol, 24S-hydroxycholesterol, 25-hydroxycholesterol, 26-hydroxycholesterol or 27-hydroxycholesterol is provided. The derivative comprises a moiety comprising a free amino, carboxylic acid, or sulfhydryl group covalently attached to the 3-OH position of the hydroxycholesterol.

Also provided is a protein conjugated to the above derivative.

Additionally, a composition is provided comprising the above protein combined with an adjuvant that can improve an antibody immune response to the protein in a vertebrate injected with the composition.

Further provided is an antibody composition comprising antibodies that specifically bind to 22-hydroxycholesterol, 24S-hydroxycholesterol, 25-hydroxycholesterol, 26-hydroxycholesterol or 27-hydroxycholesterol.

A method of making the above-described antibodies is also provided. The method comprises: (a) preparing an immunogen by conjugating the above-described derivative to a carrier protein; (b) immunizing a vertebrate with the immunogen under conditions such that the immune system of the vertebrate makes the antibodies; and (c) taking the antibodies from the vertebrate.

Additionally provided is a method of assaying for 22-hydroxycholesterol, 24S-hydroxycholesterol, 25-hydroxycholesterol, 26-hydroxycholesterol or 27-hydroxycholesterol in a fluid or tissue sample from a mammal. The method comprises combining the sample with the above-described antibodies, then determining whether the antibodies specifically bind to 22-hydroxycholesterol, 24S-hydroxycholesterol, 25-hydroxycholesterol, 26-hydroxycholesterol or 27-hydroxycholesterol from the sample. In these methods, specific antibody binding to hydroxycholesterol from the sample indicates that the hydroxycholesterol is present in the sample.

A kit for detecting and/or quantifying 22-hydroxycholesterol, 24S-hydroxycholesterol, 25-hydroxycholesterol, 26-hydroxycholesterol or 27-hydroxycholesterol is further provided. The kit comprises the above-described antibodies.

The present invention is also directed to a method of detecting an enzyme or enzymes utilized in phase II drug metabolism in a sample, where the enzyme or enzymes are capable of altering 22-hydroxycholesterol, 24S-hydroxycholesterol, 25-hydroxycholesterol, 26-hydroxycholesterol or 27-hydroxycholesterol. The method comprises combining the sample with 22-hydroxycholesterol, 24S-hydroxycholesterol, 25-hydroxycholesterol, 26-hydroxycholesterol or 27-hydroxycholesterol for a time sufficient for the enzyme or enzymes to modify the 22-hydroxycholesterol, 24S-hydroxycholesterol, 25-hydroxycholesterol, 26-hydroxycholesterol or 27-hydroxycholesterol, then assaying the sample using the above immunoassay, wherein a reduction in the amount of the 22-hydroxycholesterol, 24S-hydroxycholesterol, 25-hydroxycholesterol, 26-hydroxycholesterol or 27-hydroxycholesterol detected by the assay indicates that the sample comprises the enzyme or enzymes.

Additionally provided is a method of detecting an enzyme that synthesizes 22-hydroxycholesterol, 24S-hydroxycholesterol, 25-hydroxycholesterol, 26-hydroxycholesterol or 27-hydroxycholesterol in a sample. The method comprises combining the sample with cholesterol for a time sufficient for the enzyme to modify the cholesterol, then assaying the sample using the method of claim 43, wherein an increase in the amount of 22-hydroxycholesterol, 24S-hydroxycholesterol, 25-hydroxycholesterol, 26-hydroxycholesterol or 27-hydroxycholesterol detected by the assay indicates that the sample comprises the enzyme.

Also provided is a method of evaluating progression of multiple sclerosis in a patient. The method comprises measuring 24S-hydroxycholesterol in blood plasma or serum of the patient over time by the above-described assay method. In this method, progression of multiple sclerosis is indicated by decreasing levels of 24S-hydroxycholesterol in the blood plasma or serum over time.

A method of determining whether a treatment for multiple sclerosis in a patient is effective is also provided. The method comprises measuring 24S-hydroxycholesterol in blood plasma or serum of the patient over time by the above-described assay method. In this method, the treatment is effective if the 24S-hydroxycholesterol levels do not decrease over time.

Further provided is a method of evaluating progression of Huntington's disease in a patient. The method comprises measuring 24S-hydroxycholesterol in blood plasma or serum of the patient over time by the above-described assay method. In this method, progression of Huntington's disease is indicated by decreasing levels of 24S-hydroxycholesterol in the blood plasma or serum over time.

A method of determining whether a treatment for Huntington's disease in a patient is effective is additionally provided. The method comprises measuring 24S-hydroxycholesterol in blood plasma or serum of the patient over time by the above-described assay method. In this method, the treatment is effective if the 24S-hydroxycholesterol levels do not decrease over time.

BRIEF DESCRIPTION OF THE DRAWINGS

FIG. 1 shows a standard curve of 24S-hydroxycholesterol in an ELISA using an antiserum elicited against 3-O-succinoyl-24S-hydroxycholesterol.

DETAILED DESCRIPTION OF THE INVENTION

As used herein, the singular forms "a", "an" and "the" are intended to include the plural forms as well, unless the context clearly indicates otherwise. Additionally, the use of "or" is intended to include "and/or", unless the context clearly indicates otherwise.

The inventors have prepared antibodies to 24S-hydroxycholesterol (24HC) that have low cross-reactivity to related metabolites. The antibodies are useful reagents in rapid, specific and sensitive immunoassays for 24HC that can be utilized with standard immunoassay protocols. Based on these results, the inventors believe that effective antibodies with low cross-reactivity could also be made to other hydroxycholesterol metabolites, for example 22-hydroxycholesterol, 25-hydroxycholesterol, 26-hydroxycholesterol or 27-hydroxycholesterol. Thus, the inventors envision that any of the methods relating to 24HC that are discussed herein could also be utilized with 22-hydroxycholesterol, 25-hydroxycholesterol, 26-hydroxycholesterol or 27-hydroxycholesterol. As such, while most of the discussion below addresses only compositions and methods relating to 24HC for the sole purpose of simplifying the readability of this application, the inventors believe that any of the compositions and methods could be equally applied to 22-hydroxycholesterol, 25-hydroxycholesterol, 26-hydroxycholesterol and 27-hydroxycholesterol without undue experimentation. The inventors therefore do not disclaim, and specifically include, 22-hydroxycholesterol, 25-hydroxycholesterol, 26-hydroxycholesterol and 27-hydroxycholesterol as envisioned for any of the compositions and methods below that discuss 24HC.

Since 24HC is a hapten that is too small to illicit an antibody immune response by itself, it must be covalently coupled to a carrier protein. The 24HC-protein conjugate, when injected into a vertebrate, presents 24HC to the vertebrate's immune system as an epitope on the protein, such that antibodies are generated to the 24HC epitope. However, 24HC does not have a moiety to which it could be conveniently conjugated to a carrier protein. Therefore, a derivative of 24HC is preferably prepared that has a reactive moiety for conjugation to proteins or other reagents.

Antibodies against the closely related compound cholesterol have been prepared (Yinsong et al., 2007; Biró et al., 2007; Sato et al., 1976; Dijkstra et al., 1996). However, antibodies made by conjugation of a carrier protein to the cholesterol 3-OH moiety showed significantly diminished cholesterol binding activity when compared to antibodies made by injection of cholesterol-rich liposomes containing the adjuvant monophosphoryl lipid A (Dijkstra et al., 1996). Thus, the excellent results achieved herein in producing effective antisera against 24HC, as described in the Example below, were surprising and unexpected.

Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation (See, e.g., the website at piercenet.com/browse.cfm?fldID=4E018AA6-5056-8A76-4E57-3BC84C88A328). For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

Because the 24-hydroxyl group is the feature that distinguishes 24HC from cholesterol and other naturally occurring hydroxycholesterols (e.g., 22-hydroxycholesterol, 25-hydroxycholesterol, 26-hydroxycholesterol, 27-hydroxycholesterol), the inventors reasoned that, in spite of the poor results achieved with cholesterol in similar schemes, conjugation of the carrier protein to the 3-OH moiety would present the branched hydroxyalkane end of the 24HC molecule as an epitope of the carrier molecule to the immune system, increasing the likelihood that antibodies elicited to the 24HC would have low cross-reactivity with cholesterol and other hydroxycholesterols.

Thus, in some embodiments, a derivative of 24S-hydroxycholesterol is provided. The derivative comprises a moiety comprising a free amino, carboxylic acid, or sulfhydryl group covalently attached to the 3-OH.

In some embodiments, the moiety is a carboxylic acid. A carboxylic acid moiety can be conjugated to the 3-OH of 24HC by any method known in the art, including any method resulting in the following linkages:

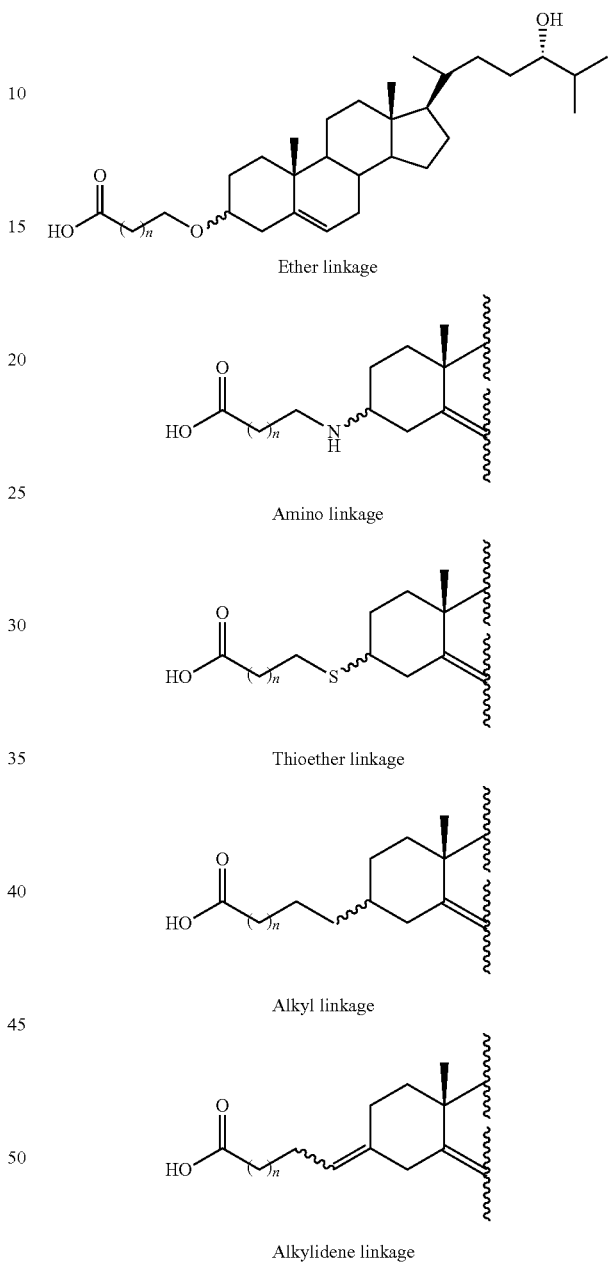

In some embodiments, the derivative is conjugated through an ester linkage, for example via the conjugation of a dicarboxylic acid to the 24HC. Any dicarboxylic acid can be utilized, here. Nonlimiting examples include oxalic acid, malonic acid, succinic acid, glutaric acid, adipic acid, pimelic acid, suberic acid, azelaic acid, sebacic acid, undecanedioic acid, dodecanedioic acid, and a phthalic acid. Methods for conjugating dicarboxylic acid derivatives to hydroxyl moieties are known in the art. See, e.g., Example. In some embodiments, the derivative consists of 3-O-succinoyl-24S-hydroxycholesterol:

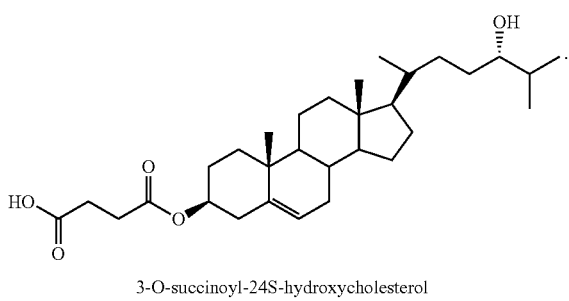 [SMILES: CC(CC[C@H](O)C(C)C)[C@H]1CCC2C3CC=C4C[C@@H](OC(=O)CCC(=O)O)CC[C@]4(C)C3CC[C@@]21C]

3-O-succinoyl-24S-hydroxycholesterol

In other embodiments, the derivative comprises 3-O-succinoyl-24S-hydroxycholesterol. Such derivatives can further encompass any other useful moiety, e.g., a moiety that further assists in conjugation to a protein. An example of the latter is an N-hydroxysuccinimide ester moiety. Thus, in some embodiments, the 3-O-succinoyl-24S-hydroxycholesterol further comprises an N-hydroxysuccinimide ester conjugated to the carboxyl group on the succinoyl moiety. In some of these embodiments, the compound is

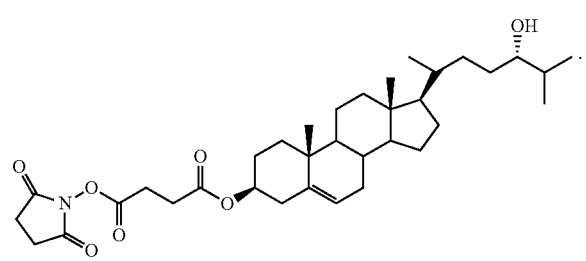 [SMILES: CC(CC[C@H](O)C(C)C)[C@H]1CCC2C3CC=C4C[C@@H](OC(=O)CCC(=O)ON5C(=O)CCC5=O)CC[C@]4(C)C3CC[C@@]21C]

cholesterol ester-BODIPY dye described in Jennings et al., 1999 can be utilized. Further, besides the various positions along the ring structure of 24S-hydroxycholesterol other than the 3β-hydroxyl position can be derivatized with a variety of tags to enable the described assay formats, so long as this attachment does not interfere with the binding of the described antibodies to the 24-OH moiety. As an example, N,N-dimethyl amino naphthalene sulfonate (dansyl) hydroxycholesterol can be utilized. Such a compound is analogous to the dansyl-cholesterol described in McIntosh et al. (2008). Compare with the compounds described in U.S. Patent Application Publication US 2008/0177059, describing BODIPY-cholesterol derivatives where the BODIPY dye is conjugated to the 22 position of cholesterol. An analogous derivative of a hydroxycholesterol would not bind to the anti-hydroxycholesterol antibodies described herein, since the antibodies are designed to bind where the BODIPY dye would be conjugated in such compounds.

Another exemplary group for signaling purposes is biotin. Thus, in some embodiments, the compound further comprises a biotin conjugated to the carboxyl group on the succinoyl moiety. Such a compound can also usefully comprise a linkage between the carboxy group, e.g., on the succinoyl moiety, and the biotin, to provide a space between the two groups, preventing steric hindrance of, e.g., a streptavidin-enzyme conjugate that binds to the biotin. The spacer can be of any length or construction known in the art. In some such embodiments, the compound is

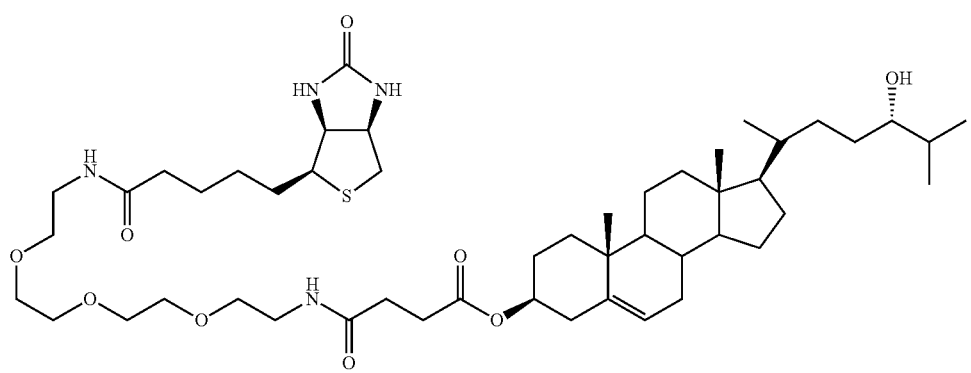

Another useful group that can be conjugated to the 3-O-succinoyl-24S-hydroxycholesterol is a moiety that can be utilized for signaling. Nonlimiting examples of signaling moieties include chromophores, fluorophores, and luminescent moieties. Derivatized cholesterol comprising fluorophores are known in the art. See, e.g., Sparrow et al. (1999) and Jennings et al. (1999). Any fluorophore can be utilized in these compositions. Additionally, such fluorescent hydroxycholesterols can utilize hydroxycholesterol derivatives other than the 3-O-succinoyl derivative. For example, a hydroxycholesterol ester-BODIPY dye, analogous to the Also provided herewith is a protein conjugated to any of the above derivatives, for example the derivative 3-O-succinoyl-24S-hydroxycholesterol. The protein can be conjugated to the derivative using any of methods known in the art, for example as discussed above, e.g., glutaraldehyde, a maleimide reagent, a carbodiimide, or an activated ester, e.g., an N-hydroxysuccinimide ester. The protein can be any protein that can usefully be utilized with the derivative. For example, the protein can be an enzyme, e.g., as a signaling molecule in enzyme immunoassays. Nonlimiting examples include horseradish peroxidase and alkaline phosphatase. The protein can also be a fluorescent protein, e.g. for the same purpose.

In other embodiments, the protein is a carrier protein for immunization of a vertebrate, to make antibodies against the derivative. Many such proteins are known in the art, e.g., keyhole limpet hemocyanin, bovine serum albumin, ovalbumin, etc. In some embodiments, a composition is provided comprising the above protein-derivative conjugate combined with an adjuvant that can improve an antibody immune response to the protein in a vertebrate injected with the composition. In certain specific embodiments the derivative is 3-O-succinoyl-24S-hydroxycholesterol.

Further provided herewith is an antibody composition comprising antibodies that specifically bind to 22-hydroxycholesterol, 24HC, 25-hydroxycholesterol, 26-hydroxycholesterol or 27-hydroxycholesterol. In some embodiments, the antibodies specifically bind to 24HC ("24HC antibodies"). In some of these embodiments, the 24HC antibodies have less than 1% cross-reactivity to cholesterol, 22-hydroxycholesterol, 25-hydroxycholesterol, 26-hydroxycholesterol, 27-hydroxycholesterol and DHEA when compared to the binding of the antibodies to 24HC. In other embodiments, the antibodies have less than 0.2% cross-reactivity to 22-hydroxycholesterol, cholesterol and DHEA when compared to the binding of the antibodies to 24S-hydroxycholesterol. In additional embodiments, the antibodies have less than 0.01% cross-reactivity to cholesterol when compared to the binding of the antibodies to 24S-hydroxycholesterol.

These antibodies can be immunoglobulins of any vertebrate species, e.g., rabbit, goat, mouse, sheep, chicken, etc. and can be polyclonal or monoclonal. They can include the Fc region or they can be Fab or Fab2 fragments. Additionally, they can be from any source, e.g., from the serum of an animal injected with an immunogen such as any of the immunogens described above, or they can be from culture or ascites as is known in the art of hybridoma technology. Alternatively, they can be from recombinant sources, e.g., as described in Winter et al., 1994, or Charlton and Porter, 2002.

A method of making 24HC antibodies is also provided. The method comprises: (a) preparing a 24HC immunogen by conjugating any of the above-described 24HC derivatives to a carrier protein; (b) immunizing a vertebrate with the immunogen under conditions such that the immune system of the vertebrate makes antibodies to 24HC; and (c) taking the 24HC antibodies from the vertebrate. In some embodiments, the derivative is 3-O-succinoyl-24S-hydroxycholesterol. The carrier protein can be any of those discussed above. In some of these embodiments, the carrier protein is keyhole limpet hemocyanin, bovine serum albumin (BSA) or ovalbumin.

These methods are not narrowly limited to any particular set of vertebrates. In some embodiments, the vertebrate is a rabbit, a goat, a mouse, a chicken, or a sheep. Additionally, the antibodies taken from the vertebrate can be polyclonal antibodies or monoclonal antibodies.

The 24HC antibodies described above can be utilized to detect 24HC by any immunoassay known in the art. Thus, additionally provided herein is a method of assaying for 24HC in a fluid or tissue sample from a mammal. The method comprises combining the sample with 24HC antibodies, then determining whether the antibodies specifically bind to 24HC from the sample. In these methods, specific antibody binding to 24HC from the sample indicates that 24HC is present in the sample.

The sample can be from any fluid or tissue from the mammal. In some embodiments, the sample is from cerebrospinal fluid, blood (e.g., whole blood, serum or plasma), or brain tissue, since those samples are known to contain 24HC.

The sample can be from any mammal. In some embodiments, the sample is from a human, e.g., a human without any apparent disease, or a human that has, or is suspected of having, cognitive impairment, Huntington's disease, Alzheimer's disease, or multiple sclerosis, which are known to affect the amount of 24HC in cerebrospinal fluid, plasma, and/or brain tissue.

Depending on the assay and sample, the sample can be used directly in the assay, for example after dilution in a buffer, or the sample can be at least partly purified to eliminate substances that might interfere with the assay. Numerous such purification procedures are known in the art. For example, the sample could be solvent-extracted or subjected to chromatography, e.g., through a C18 column, before use in the assay. In some protocols, the eluate from the chromatographic procedure or extraction is dried and resuspended in a buffer that does not interfere in the assay. See, e.g., Axelson (1991). Such a drying and resuspension procedure can also be used to concentrate the sample if there is concern that the amount of the 24HC is below the level of immunoassay detection.

These assay methods can comprise any immunoassay known in the art. In some embodiments, the assay is performed in a liquid phase. In other embodiments, the assay is performed on a solid phase, e.g., on a bead or a microplate, for example a 96 well microtiter plate. Nonlimiting examples of immunoassays useful in these methods are a radioimmunoassay (see, e.g., U.S. Pat. No. 4,081,525), a Luminex® assay (see, e.g., Wong et al., 2008), a microarray assay, a fluorescence polarization immunoassay (see, e.g., U.S. Pat. No. 4,585,862), an immunoassay comprising a Förster resonance energy transfer (FRET) signaling system (see, e.g., Blomberg et al., 1999; Mayilo et al., 2009), and enzyme immunoassay (a.k.a. enzyme linked immunosorbent assay [ELISA]). As is well known in the art, in ELISA, an enzyme combined with a substrate that becomes colored upon reaction with the enzyme provides the signal to quantify the antigen in the sample. See, e.g., O'Beirne and Cooper, 1979.

Table 1 provides a summary of various immunoassays that can be utilized for detection of the hydroxycholesterols to which antibodies are provided herewith. The general features of these assays are known in the art.

TABLE 1

| Detection Method | 24-OH cholesterol probe | Antibody | Other components |
| --- | --- | --- | --- |
| Scintillation proximity assay | Radio-iodinated | Immobilized | Scintillant-coated plate or bead |
| Fluorescence polarization assay | Fluorescently-labeled | Unlabeled | |
| Homogeneous time-resolved fluorescence assay | Allophyocyanin-labeled | Europium cryptate-labeled | |

TABLE 1-continued

| Detection Method | 24-OH cholesterol probe | Antibody | Other components |
| --- | --- | --- | --- |
| Amplified luminescence assay (ALPHAScreen) | Biotin-labeled | Acceptor bead-labeled | Streptavidin-labeled donor bead |
| Enzyme complementation assay | Inactive enzyme donor-labeled | Immobilized | Enzyme acceptor, enzyme substrate (e.g. fluorogenic β-galactosidase substrate) |
| Electrochemiluminescence assay | Ruthenium-labeled | Immobilized | Carbon electrode plates, chemical substrate and electrical stimulation |

Any ELISA known in the art as useful for hapten detection can be utilized for the instant assays. ELISA for haptens generally utilize a competitive format, i.e., where the hapten (here, 24HC) in the sample competes with a labeled hapten (e.g., a biotin-hapten or enzyme-hapten conjugate) for anti-hapten antibody binding sites such that less labeled hapten is bound when there is more hapten in the sample. Thus, in these competitive assays, an increasing amount of hapten in the sample results in less enzyme bound to the solid phase, and consequently less colored signal. In such competitive assays, as defined herein, the sample can be added with the labeled hapten to compete directly for antibody binding sites, or the sample and labeled hapten can be added sequentially such that the labeled hapten simply binds where the sample hapten is not bound.

In some embodiments, the ELISA is a direct competitive ELISA, defined herein as where the 24HC hapten is directly bound to the signaling enzyme, or an indirect competitive ELISA, where the enzyme is bound to another molecule, e.g., a second antibody, or streptavidin.

The ELISA assays provided herein can take any format known in the art. In some embodiments, a 24HC conjugate (e.g., 24HC-BSA or 24HC-polylysine) is bound to the solid phase. In these assays, the 24HC antibody is added with the sample. Here, the 24HC in the sample competes with the solid phase-bound 24HC conjugate for antibody binding sites such that less antibody binds to the solid phase when there is more 24HC in the sample. After washing, the amount of 24HC antibody bound to the solid phase is measured, e.g., by utilizing in the competitive step a 24HC antibody-enzyme conjugate, or by adding a second antibody-enzyme conjugate that binds to the bound 24HC antibody. A myriad of particular assays for 24HC with this configuration can be devised without undue experimentation.

In other embodiments, the 24HC antibodies are bound to the solid phase, either directly or indirectly, the latter being where the solid phase is coated with an anti-antibody (for example goat antibodies that bind to rabbit IgG antibodies [goat anti-rabbit IgG]) and the 24HC antibodies are bound to the anti-antibody. The anti-antibodies are also known as "second antibodies". In these assays, the sample and a labeled hapten is added to the solid phase to compete with antibody binding sites on the coated solid phase. After washing, the signal is generated, which measures the amount of labeled hapten that is bound to the solid phase. Numerous particular assays for 24HC with this configuration can be devised without undue experimentation.

An illustration of the latter assay, where the 24HC antibodies are bound to the solid phase, is provided in the Example below. That assay comprises:

a. noncovalently binding the second antibodies to the solid phase;

b. adding the 24S-hydroxycholesterol antibodies to the solid phase under conditions such that the second antibodies specifically bind to the 24S-hydroxycholesterol antibodies;

c. adding the sample and a biotinylated 24S-hydroxycholesterol to the solid phase under conditions such that the biotinylated 24S-hydroxycholesterol binds to binding sites on the 24S-hydroxycholesterol antibodies where 24S-hydroxycholesterol in the sample do not bind;

d. adding an avidin-enzyme conjugate to the solid phase under conditions such that the avidin-enzyme conjugate specifically binds to the biotinylated 24S-hydroxycholesterol that bound in step c.;

e. adding a substrate to the enzyme in the avidin-enzyme conjugate, wherein the substrate is converted to a colored product that absorbs light at a specified wavelength in proportion to the amount of the enzyme bound to the solid phase;

f. measuring the absorbance of light at the specified wavelength, wherein the absorbance is inversely proportional to the amount of 24S-hydroxycholesterol present in the sample.

With any of the above-described immunoassays, 24HC in the sample is quantified by comparing the signal generated (e.g., fluorescence in the FRET and fluorescence polarization assays, radioactivity in radioimmunoassays, absorbance in ELISAs) in the assay where the sample is added to the signal generated in assays where a known amount of 24HC is added, i.e., comparing the sample signal to a standard curve.

The present invention is also directed to a kit for detecting and quantifying 24HC. The kit comprises 24HC antibodies. In some embodiments, the kit further comprises a protein conjugate or a biotin conjugate of 24S-hydroxycholesterol. In other embodiments, the kit further comprises a solid phase, e.g., beads or a microtiter plate. In these embodiments, the solid phase comprises a noncovalently bound protein, where the bound protein is an antibody or a protein conjugate of 24S-hydroxycholesterol. In various embodiments, the kit further comprises an enzyme. Examples of such enzymes are alkaline phosphatase or horseradish peroxidase, covalently bound to 24HC or an antibody (e.g., a 24HC antibody or a second antibody). In additional embodiments, the kit further comprises 24HC, for example for use in a standard curve.

As discussed in the Background section of this application, 24HC is a substrate for various cytosolic sulfotransferases (SULT) and UDP-glucuronosyltransferases (UGT). Sulfation involves the transfer of the sulfonate group of the obligate sulfonate donor 3'-phosphoadenosine-5'-phosphosulfate (PAPS) to an acceptor compound, usually possessing a hydroxyl group, to form a sulfate ester. Typically, [$^{35}$S] PAPS is employed in the SULT assay. The assay is often terminated by chloroform extraction and the sulfated products in the aqueous phase are resolved by thin layer chromatography (TLC) on silica gel TLC plates and detected by autoradiography. However, to define the sites of sulfate conjugation, an LC-MS/MS approach is usually required. Nonradioactive reactions can be run in parallel with reactions containing [$^{35}$S]PAPS and monitored by TLC. The non-radioactive reactions are extracted with chloroform and the water phase loaded onto a Sep-Pak cartridge, washed with water and eluted with MeOH. The eluates can be concentrated by evaporation under a stream of N2. Identification of the sulfated compounds is by HPLC-mass spectroscopy using, for example, a Sciex API-4000 Triple Quadrupole mass spectrometer with two Perkin Elmer series 200 micropumps (Perkin Elmer Life and Analytical Sciences, Boston, Mass.) and a Synergi Fusion (100×2 mm ID) analytical C-18 column with a C-18 guard column (Phenomenex).

In an analogous manner, the glucuronidation reaction can be monitored as the transfer of the glucuronosyl group from UDP[U-$^{14}$C] glucuronic acid to the target substrate. HPLC on a polar amino-cyano bonded phase column is employed to separate radioactive glucuronides from unmetabolized UDP[U-$^{14}$C]glucuronic acid (Coughtrie et al., 1986).

The immunoassays described herein can be utilized to detect activity of UGT and SULT or any other enzymes that alter a hydroxycholesterol such that it no longer binds to the antibodies described herein. For example, the extracerebral double conjugation of 24-OH cholesterol to generate (24S)-24-hydroxycholesterol 3-sulfate, 24-glucuronide can be analyzed by immunoassay using the immunoassays of the present invention in combination with, e.g., immunoassays selective for sulfation, or alternatively in combination with techniques allowing the selective separation of the sulfated form of the analyte from the nonsulfated form. For example, approaches that allow the selective precipitation of the sulfated form of the analyte, as described in U.S. patent application Ser. No. 12/806,950, filed Aug. 24, 2010, would facilitate the analysis. Such an approach eliminates the need for the time-consuming analysis of UGT and SULT activity now utilized, as described above. The potential for high throughput analysis as can be employed with the immunoassays described herein, as well as the high sensitivity of the immunoassays, provides opportunities to utilize these immunoassays to monitor phase II drug metabolism assays and screen drugs and new chemical entities for their capacity to modulate phase II enzyme activity in native or recombinant fractions.

Thus, the present invention is also directed to a method of detecting an enzyme or enzymes utilized in phase II drug metabolism in a sample, where the enzyme or enzymes are capable of altering 22-hydroxycholesterol, 24S-hydroxycholesterol, 25-hydroxycholesterol, 26-hydroxycholesterol or 27-hydroxycholesterol. The method comprises combining the sample with 22-hydroxycholesterol, 24S-hydroxycholesterol, 25-hydroxycholesterol, 26-hydroxycholesterol or 27-hydroxycholesterol for a time sufficient for the enzyme or enzymes to modify the 22-hydroxycholesterol, 24S-hydroxycholesterol, 25-hydroxycholesterol, 26-hydroxycholesterol or 27-hydroxycholesterol, then assaying the sample using any of the above-described immunoassays. In these methods, a reduction in the amount of the 22-hydroxycholesterol, 24S-hydroxycholesterol, 25-hydroxycholesterol, 26-hydroxycholesterol or 27-hydroxycholesterol detected by the assay indicates that the sample comprises the enzyme or enzymes.

In some embodiments of these methods, the enzyme is a cytosolic sulfotransferase, a UDP-glucuronosyltransferase, or a combination thereof. In certain specific embodiments, the enzyme or enzymes are capable of altering 24S-hydroxycholesterol.

These methods can also be utilized to determine whether a compound is capable of modulating the enzyme or enzymes, or reducing their expression (the latter case where the sample includes cells that produce the enzyme or enzymes). In these embodiments, the compound is added to the sample with the enzyme or enzymes. If the compound modulates the enzyme or enzymes, the difference in the amount of the 22-hydroxycholesterol, 24S-hydroxycholesterol, 25-hydroxycholesterol, 26-hydroxycholesterol or 27-hydroxycholesterol detected by the immunoassay when the compound is included vs. when the compound is excluded indicates that the compound modulates the enzyme. For example, if the compound inhibited or reduced the expression of the enzyme or enzymes, less of the hydroxycholesterol would be altered, and the immunoassay would show more of the hydroxycholesterol present than when the compound was not included with the enzyme or enzymes. Conversely, if the compound enhanced the activity, or increased expression of the enzyme or enzymes, more of the hydroxycholesterol would be altered, and the immunoassay would show less of the hydroxycholesterol present than when the compound was not included with the enzyme or enzymes.

In a specific embodiment, inhibitor screening for UGT and SULT can be accomplished using a competitive binding assay format. A decrease in the formation of 24-OH cholesterol metabolite compared to the vehicle control is used to calculate an IC50 value of the test agent. For example, a UGT isozyme inhibition assay can be performed as follows: The UGT substrate, 24-OH cholesterol, is incubated with a cDNA-expressed human UGT isoform, such as UGT1A1, as well as with UDP-glucuronic acid (UDPGA), and a range of test compound concentrations (typically 0.4-100 µM) for 30 min at 37° C. Optionally, a microsomal preparation can also be incorporated to enhance enzyme activity. Due to the luminal location of the UGT's within the endoplasmic reticulum of microsomal preparations, the passage of the water soluble cofactor UDPGA to the active site can be challenging. In order to circumvent this latency phenomenon, the pore forming agent, alamethicin, can be included to improve access to the active site. At the end of the incubation period, the formation of the metabolite, 24-OH cholesterol 3-glucuronide is monitored by immunoassay, using antibodies of the present invention, at each of the test compound concentrations. A decrease in the formation of the metabolite compared to vehicle control is used to calculate an IC50 value of the inhibitor (test compound concentration which produces 50% inhibition of UGT1A1). The selective UGT1A1 inhibitor, silybin, can be used as the positive control inhibitor in the described assay.

These methods can be further utilized to quantify the enzyme or enzymes, e.g., by comparing the reduction in the amount of the 22-hydroxycholesterol, 24S-hydroxycholesterol, 25-hydroxycholesterol, 26-hydroxycholesterol or 27-hydroxycholesterol detected by the assay in the sample with the reduction in the amount of 22-hydroxycholesterol, 24S-hydroxycholesterol, 25-hydroxycholesterol, 26-hydroxycholesterol or 27-hydroxycholesterol present when treated by a standard amount of the enzyme or enzymes.

The above-described immunoassays can also be utilized in a method to detect an enzyme that synthesizes 22-hydroxycholesterol, 24S-hydroxycholesterol, 25-hydroxycholesterol, 26-hydroxycholesterol or 27-hydroxycholesterol in a sample. The method comprises combining the sample with cholesterol for a time sufficient for the enzyme to modify the cholesterol, then assaying the sample using any of the above-described immunoassays. In these methods, an increase in the amount of 22-hydroxycholesterol, 24S-hydroxycholesterol, 25-hydroxycholesterol, 26-hydroxycholesterol or 27-hydroxycholesterol detected by the assay indicates that the sample comprises the enzyme. In some embodiments of these methods, the enzyme is CYP46 and the assay detects 24S-hydroxycholesterol.

In certain embodiments of these methods, the enzyme in the sample is quantified by comparing the increase in the amount 22-hydroxycholesterol, 24S-hydroxycholesterol, 25-hydroxycholesterol, 26-hydroxycholesterol or 27-hydroxycholesterol detected by the assay in the sample with the increase in the amount of 22-hydroxycholesterol, 24S-hydroxycholesterol, 25-hydroxycholesterol, 26-hydroxycholesterol or 27-hydroxycholesterol present when cholesterol is treated by a standard amount of the enzyme.

Since reductions in plasma 24HC levels are associated with certain diseases, in particular multiple sclerosis and Huntington's disease (see Background above), the immunoassays described herein can be used to monitor the progression and efficacy of treatment for those diseases.

Thus, in some embodiments, a method of evaluating progression of multiple sclerosis in a patient is provided. The method comprises measuring 24S-hydroxycholesterol in blood plasma or serum of the patient over time by the above-described assay method. In this method, progression of multiple sclerosis is indicated by decreasing levels of 24S-hydroxycholesterol in the blood plasma or serum over time.

Also provided is a method of determining whether a treatment for multiple sclerosis in a patient is effective is also provided. The method comprises measuring 24S-hydroxycholesterol in blood plasma or serum of the patient over time by the above-described assay method. In this method, the treatment is effective if the 24S-hydroxycholesterol levels do not decrease over time.

A method of evaluating progression of Huntington's disease in a patient is also provided. The method comprises measuring 24S-hydroxycholesterol in blood plasma or serum of the patient over time by the above-described assay method. In this method, progression of Huntington's disease is indicated by decreasing levels of 24S-hydroxycholesterol in the blood plasma or serum over time.

Additionally provided is a method of determining whether a treatment for Huntington's disease in a patient is effective is additionally provided. The method comprises measuring 24S-hydroxycholesterol in blood plasma or serum of the patient over time by the above-described assay method. In this method, the treatment is effective if the 24S-hydroxycholesterol levels do not decrease over time.

Preferred embodiments are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example. Preparation of Antisera to 24S-Hydroxycholesterol and its Use in Immunoassay Detection of Same Since 24S-hydroxycholesterol (24HC) is a hapten that is too small to illicit an antibody immune response by itself, it must be covalently coupled to a carrier protein, which, when injected in a vertebrate, presents 24HC to the vertebrate's immune system as an epitope on the protein, such that antibodies are generated to the 24HC epitope. However, 24HC does not have a moiety to which it could be conveniently conjugated to a carrier protein. Therefore, the 3-O-succinoyl derivative of 24HC was prepared as follows:

Preparation of 3-O-Succinoyl-24S-Hydroxycholesterol

To 24HC (21 mg [0.052 mmol]) in 3 mL dry pyridine was added succinic anhydride (10 mg [0.10 mmol]). The mixture was heated under Ar at 80° C. for 3 days. The reaction was then diluted with ethyl acetate and washed with 1M HCl and brine. Flash chromatography (2% MeOH/CH2Cl2) yielded 12 mg (46%) of product. This scheme is illustrated below:

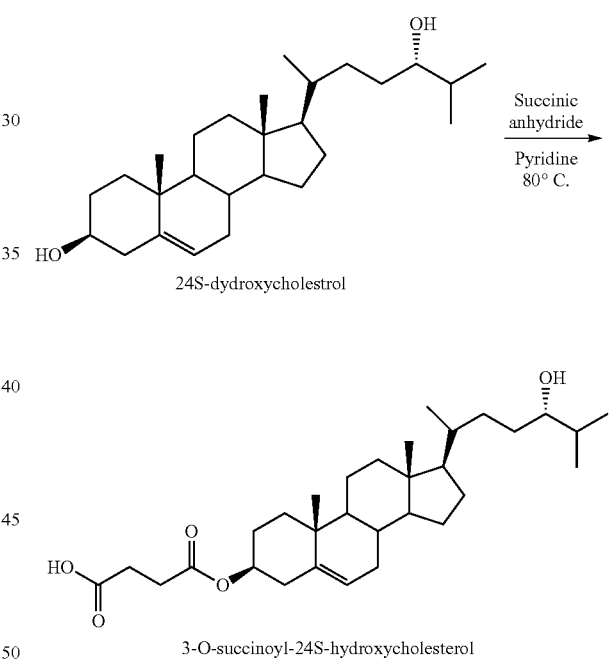

An activated ester of 3-O-succinoyl-24S-hydroxycholesterol, 3-O-succinoyl-24S-hydroxycholesterol N-hydroxysuccinimide ester, was then prepared as follows:

Preparation of 3-O-Succinoyl-24(S)-Hydroxycholesterol N-Hydroxysuccinimide Ester To 3-O-Succinoyl-24(S)-hydroxycholesterol (9.2 mg [0.018 mmol]) and N-hydroxysuccinimide (NHS) (2.3 g [20 mmol]) in 2 mL dry THF was added 1-Ethyl-3-(3-dimethylaminopropyl)carbodiimide (3.9 mg [0.020 mmol]). The reaction mixture was stirred overnight at room temperature. It was then diluted with diethyl ether and washed with water and brine. Flash chromatography (100% CH2Cl2) gave 4.7 mg (43%) of the desired product. This scheme is illustrated below:

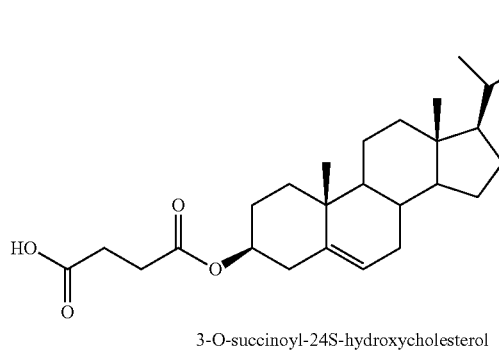

3-O-succinoyl-24S-hydroxycholesterol

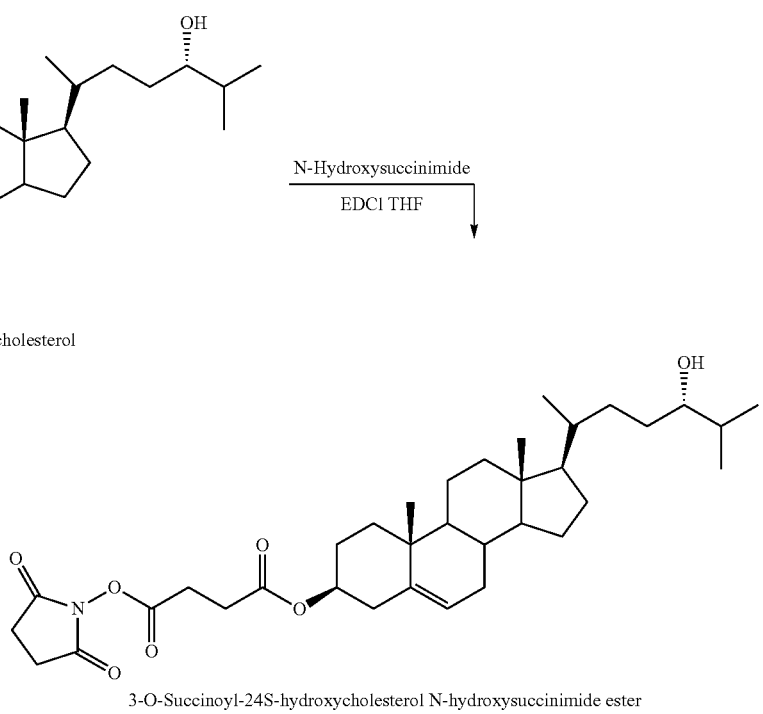

3-O-Succinoyl-24S-hydroxycholesterol N-hydroxysuccinimide ester

The 3-O-Succinoyl-24S-hydroxycholesterol NHS ester was then conjugated to the carrier protein keyhole limpet hemocyanin (KLH) as follows:

Preparation of 3-O-Succinoyl-24S-Hydroxycholesterol-KLH

1. Ten mg of KLH lyophilized in 0.1 M sodium phosphate, 0.15 M NaCl; pH 7.2 (Pierce product #77600) was resuspended in 1 mL water.
2. Four mg of the 3-O-succinoyl-24S-hydroxycholesterol NHS ester was resuspended in 100 μL of dimethyl sulfoxide.
3. The 3-O-succinoyl-24S-hydroxycholesterol NHS ester solution was added dropwise to the KLH solution 10 μL at a time. After 70 μL was added, a precipitate was observed and 0.5 mL of H$_2$O was added to clear the solution before adding the remainder of the NHS ester.
4. The solution was gently mixed on a tilting platform mixer for 1 hour at room temperature and then transferred to a dialysis bag (1 kD pore size). The solution was dialysed for 4.5 hours at room temperature against 1 liter 0.1 M sodium phosphate, 0.15 M NaCl; pH 7.2. The dialysis buffer was changed and dialysis continued overnight. The dialysis buffer was changed one more time and dialysis was completed after an additional 6.5 hours.
5. The final solution was brought to 10 mL final volume and aliquoted.

This 3-O-Succinoyl-24S-hydroxycholesterol-KLH conjugate was used as an immunogen to elicit antibodies in rabbits by the following protocol:

Immunization Protocol

1. Female New Zealand White rabbits were immunized intradermally with 500 μg of 24S-hydroxycholesterol—KLH conjugate in PBS. The immunogen with complete adjuvant was prepared by mixing 0.5 mL of 1 mg/mL hydroxycholesterol—KLH conjugate with 0.5 mL Freund's complete adjuvant and emulsifying by passage through glass syringes.
2. Prebleeds were collected 1 day prior to the first immunization.
3. Rabbits were injected 1 mL of immunogen intradermally over 10 sites on day 1.
4. Immunogen with incomplete adjuvant was prepared by mixing 0.5 mL of 1 mg/mL 24S-hydroxycholesterol—KLH conjugate with 0.5 mL Freund's incomplete adjuvant and emulsifying by passage through glass syringes.
5. Rabbits were injected with 1 mL of this immunogen intradermally over 10 sites on day 21, 42 and 63.
6. Rabbits were bled on Day 74 and Day 77.
7. Rabbits were injected with 1 mL of immunogen with incomplete adjuvant (described in 4. above) intradermally over 10 sites on day 84.
8. Rabbits were bled on Day 95.
11. Rabbits were injected with 1 mL of immunogen with incomplete adjuvant intradermally over 10 sites on day 105.
12. Rabbits were bled on Day 116.
14. Rabbits were injected with 1 mL of immunogen with incomplete adjuvant intradermally over 10 sites on day 126.
15. Rabbits were bled on Day 136 and 138.

In some cases, the antisera was screened in an ELISA using 96 well microtiter plates coated with a 3-O-succinoyl-24S-hydroxycholesterol linked to bovine serum albumin (BSA), prepared by conjugating the 3-O-succinoyl-24S-hydroxycholesterol NHS ester described above to BSA by the method described above with KLH. This screening protocol is as follows:

Antisera Screening Assay Using 24S-Hydroxycholesterol—BSA 1. 100 μL of 24(S)Hydroxycholesterol—BSA conjugate was coated to plate at a concentration of 1 μg/mL in 10 mM sodium phosphate buffer pH 8.0 overnight at 4° C. Plates were blocked for 1 hour in 10 mM sodium phosphate, 150 mM sodium chloride, 1% BSA buffer.
2. Rabbit antisera was serially diluted in 100 mM phosphate, 150 mM NaCl, pH 7.2 assay buffer and 100 μL of each dilution was transferred to individual wells on a 96 well plate. The plate was incubated at room temperature for 1 h with orbital shaking.

3. The plates were washed 4 times with 300 μL of 50 mM Tris, 100 mM NaCl, 0.05% Tween-20 buffer.

4. Goat anti-rabbit—horseradish peroxidase (HRP) conjugate was diluted to 200 ng/mL and 100 μL was added to each well and incubated for 1 hour at room temperature.

Preparation of Biotinylated 3-O-Succinoyl-24S-Hydroxycholesterol

To 3-O-Succinoyl-24S-hydroxycholesterol N-hydroxysuccinimide ester (4.7 mg [7.8 μmol]) in 1 mL dry CH2C12 was added biotinyl-3,6,9-trioxaundecanediamine (3.3 mg [7.8 μmol]). After stirring overnight at room temperature, the mixture was subjected to flash chromatography (10% MeOH/CH2C12) to yield 4.4 mg (62%) of product. This scheme is illustrated below:

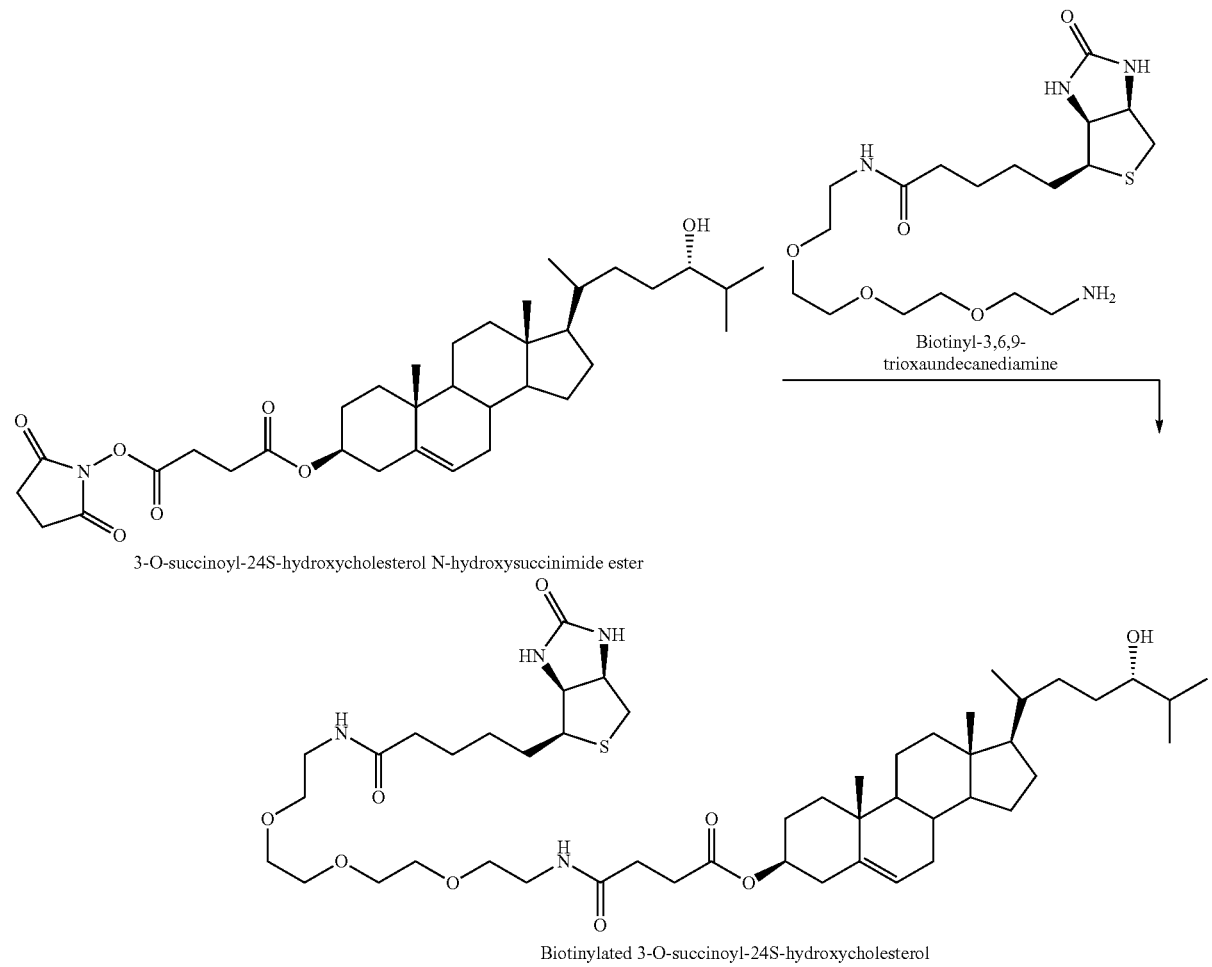

5. The plate was washed 4 times with 300 μL of 50 mM Tris, 100 mM NaCl, 0.05% Tween-20 buffer to remove excess HRP conjugate. 100 μL of TMB substrate solution was added to each well. The plates were incubated at room temperature for 30 min. An HRP-catalyzed reaction generates a blue color in the solution.

6. After color development, 50 μL of 1N HCl stop solution is added to each well to stop the substrate reaction. The HCl solution converts the blue color to yellow. The resulting yellow color was read at 450 nm. The intensity of yellow color (read as absorbance at 450 nm) is directly proportional to the amount of anti-24S-hydroxycholesterol antibody in the in the sample.

In other cases, the antisera were screened using an assay that employs a biotinylated 3-O-succinoyl-24(S)-hydroxycholesterol, which was prepared as follows:

The screening assay using the biotinylated 3-O-succinoyl-24S-hydroxycholesterol reagent was as follows:

Antisera Screening Assay Using Biotinylated 24HC

1. A microtiter plate (96 well) was coated with goat anti-rabbit IgG antibody. Rabbit antiserum to 24HC (100 μl), serially diluted in 100 mM phosphate, 150 mM NaCl, pH 7.2 assay buffer, was added to 100 μL biotinylated 24HC diluted in the same buffer before adding to the microtiter plate wells coated with a goat anti-rabbit IgG antibody. The plate was incubated at room temperature for 1 hour with orbital shaking. During this incubation the antibody binds the biotinylated 24S-hydroxycholesterol and becomes bound to the goat anti-Rabbit IgG coated on the plate surface.

2. The plate is washed 4 times with 300 μL of 50 mM Tris, 100 mM NaCl, 0.05% Tween-20 buffer. After washing only bound 24S-hydroxycholesterol or bound biotinylated 24S-hydroxycholesterol remains.

3. Streptavidin conjugated to horseradish peroxidase was diluted to working concentration in 100 mM phosphate, 150 mM NaCl, pH 7.2 assay buffer and 200 μL was added to each well to allow detection of the bound biotinylated 24S-hydroxycholesterol. The plate was incubated at room temperature for 30 minutes.

4. The plate was washed 4 times with 300 μL of 50 mM Tris, 100 mM NaCl, 0.05% Tween-20 buffer to remove excess HRP conjugate. TMB substrate solution (200 μL) is added to each well. The plates were incubated at room temperature for 30 min.

5. After color development, 50 μL of 1N HCl stop solution is added to each well to stop the substrate reaction. The resulting yellow color was read at 450 nm. The intensity of yellow color is directly proportional to the amount of anti-24S-hydroxycholesterol antibody in the in the sample.

The following protocol was used to detect varying amounts of 24HC to create a standard curve for 24HC:

24HC Enzyme Immunoassay Protocol

1. Known concentrations of 24HC were prepared in 100 mM phosphate, 150 mM NaCl, 1% BSA, pH 7.2 assay buffer containing biotinylated 24HS (described above) and added to wells of a 96 well microtiter plate that were coated with a goat anti-rabbit IgG antibody. Rabbit polyclonal antibody to 24HC was diluted to a limiting concentration in 100 mM Tris, 150 mM NaCl, 1% BSA buffer and 100 μL was added to each well. The plate was incubated at room temperature for 1 hour with orbital shaking. During this incubation the anti-24HC antibody binds to the goat anti-rabbit IgG antibody on the plate. Also, the 24HC standard competes with the biotinylated 24HC for anti-24HC antibody binding sites. Thus, with more 24HC standard, less biotinylated 24HC binds to the antibody binding sites on the plate.

2. Following this incubation, the plate was washed 4 times with 300 μL of 50 mM Tris, 100 mM NaCl, 0.05% Tween-20 buffer. After washing, bound 24HC or bound biotinylated 24HC is bound to the binding sites on the anti-24HC antibodies.

3. Streptavidin conjugated to HRP (200 μL), diluted in 100 mM phosphate, 150 mM NaCl, 1% BSA, pH 7.2 assay buffer, was then added to each well to allow detection of the biotinylated 24HC. The plate was then incubated at room temperature for 30 minutes.

4. The plate was then washed 4 times with 300 μL of 50 mM Tris, 100 mM NaCl, 0.05% Tween-20 buffer to remove excess streptavidin-HRP conjugate. TMB substrate solution (200 μL) is added to each well. The plates were incubated at room temperature for 30 min.

5. After color development, 50 μL of 1N HCl stop solution is added to each well to stop the substrate reaction. The resulting yellow color was read at 450 nm. The resulting yellow color was read at 450 nm. The intensity of yellow color is inversely proportional to the concentration of 24HC that was added to the well.

A typical standard curve for this assay is shown in FIG. 1. The multiple regression line shown therein has an $R^2$ of 0.996. The detectable range for 24HC for this assay is as shown is 1.56-100 ng/mL. The total assay time is 2 h.

Cross-reactivity of the antisera tested above (Day 77 bleed, rabbit #72) to the following structurally similar molecules was determined:

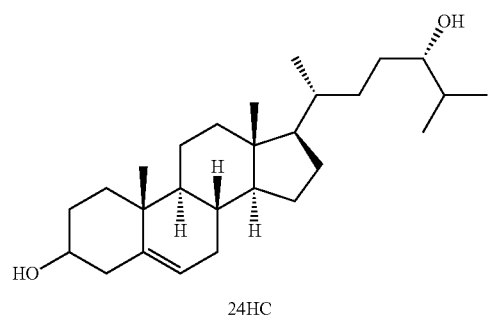

24HC

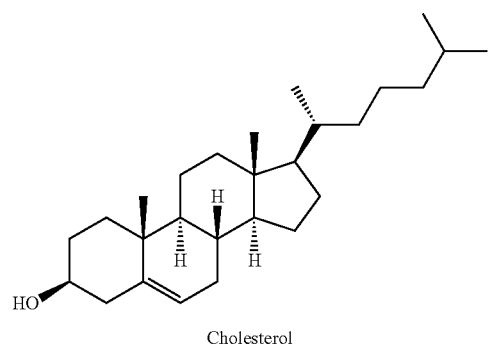

Cholesterol

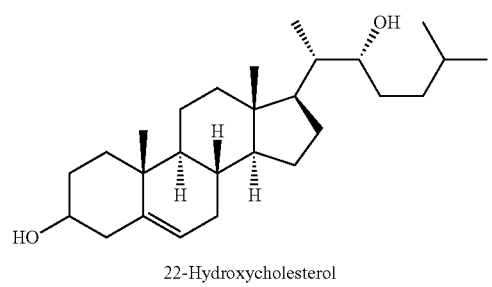

22-Hydroxycholesterol

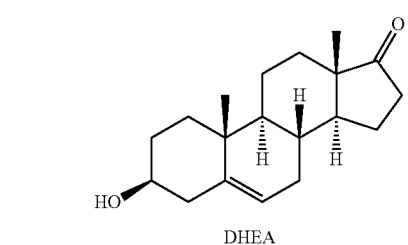

DHEA

Results of that cross-reactivity study are shown in Table 2:

TABLE 2

| Molecule | % Cross reactivity |
|---|---|
| Cholesterol | <0.001 |
| 22-Hydroxycholesterol | 0.15 |
| DHEA | 0.05 |

This study shows that the cross-reactivity to these structurally similar compounds is minimal.

Cross-reactivities of antisera taken from another rabbit at Day 77 (rabbit #71), subjected to the same immunization protocol, as well as a repeat of the rabbit #72 antisera, were also determined. The results are shown in Table 3.

TABLE 3

| Molecule | Bleed #71 % Cross reactivity | Bleed #72 % Cross reactivity |
|---|---|---|
| Cholesterol | 0.002 | 0.003 |
| 22-Hydroxycholesterol | 0.020 | 0.11 |
| 25-Hydroxycholesterol | 0.19 | 0.725 |
| 27-Hydroxycholesterol | 0.022 | <0.001 |
| DHEA | 0.015 | 0.018 |

As with the assay described in Table 2, the cross-reactivities of structurally similar compounds with these two antisera were minimal. The small differences in cross-reactivities described in Table 1 and the "Bleed #72" data in Table 3 represent variation in the assay.

Based on the studies described in this Example, the antisera to 24HC is useful for quantifying 24HC in, e.g., plasma, cerebrospinal fluid, and tissue.

REFERENCES

Alexandrov et al., 2005, Neuroreport. 21:909-13.
Axelson, 1991, J. Lipid Res. 32:1441-8.
Björkhem et al., 2009, Mol. Aspects Med. 30:171-9.
Biró et al., 2007, J. Lipid Res. 48:19-29.
Blomberg et al., 1999, Clin. Chem. 45:855-61.
Bretillon et al., 2000, J. Lipid Res. 41:840-5.
Bryleva et al., 2010, Proc. Natl. Acad. Sci. USA 107:3081-6.
Burkard et al., 2004, J. Lipid Res. 45:776-81.
Charlton and Porter, 2002, Meth. Mol. Biol. 178:159-71.
Cook et al., 2009, Drug Metab Dispos. 37:2069-78.
Coughtrie et al., 1986, Anal. Biochem. 59:198-205.
DeBarber et al., 2008, Anal. Biochem. 381:151-3.
Dijkstra et al., 1996, J. Immunol. 157:2006-13.
Garcia et al., 2009, J. Mol. Neurosci. 39:342-5.
Hudry et al., 2010, Mol. Ther. 18:44-53.
Irizarry, 2004, NeuroRx 1:226-34.
Jennings et al., 1999, Am. J. Physiol. 277:G-1017-26.
Kölsch et al., 2004, Neurosci. Lett. 368:303-8.
Koschack et al., 2009, Neurobiol. Aging 30:898-902.
Leoni, 2009, Scand. J. Clin. Lab Invest. 69:22-5.
Leoni et al., 2008, Brain 131:2851-9.
Leoni et al., 2010, Biochem. Soc. Trans. 38:1021-5.
Lütjohann and von Bergmann, 2003, Pharmacopsychiatry 36 Suppl. 2:S102-6.
Lütjohann et al., 1996, Proc. Natl. Acad. Sci. USA 93:9799-804.
Lütjohann et al., 2000, J. Lipid Res. 41:195-8.
Masterman et al., 2002, Neurosci. Lett. 331:163-6.
Mayilo et al., 2009, Analytica Chimica Acta 646:119-22.
Mcintosh et al, 2008 Chapter 1. Fluorescent Sterols for the Study of Cholesterol Trafficking in Living Cells, pp. 1-20 In: Probes and Tags to Study Biomolecular Functions: For Proteins, RNA and Membranes, Lawrence W. Miller (Editor), Wiley Press.
O'Beirne and Cooper, 1979, J. Histochem. Cytochem. 27:1148-62.
Papassotiropoulos et al., 2002, J. Psychiatr. Res. 36:27-32.
piercenet.com/browse.cfm?fldID=4E018AA6-5056-8A76-4E57-3BC84C88A328.
Sato et al., 1976, Biomedicine. 15:385-9.
Shafaati et al., 2007, Neurosci. Lett. 425:78-82.
Solomon et al., 2009, Neurosci. Lett. 462:89-93.
Sparrow et al., 1999, J. Lipid Res. 40:1747-57/
Teunissen et al., 2003, Neurosci. Lett. 347:159-62.
Teunissen et al., 2005, Lancet Neurol. 4:32-41.
Valenza et al., 2007, Hum. Mol. Genet. 16:2187-98.
Vega and Weiner, 2007, J. Mol. Neurosci. 33:51-5.
Winter et al., 1994, Ann. Rev. Immunol. 12:433-55.
Wong et al., 2008, Cancer Epidemiol. Biomarkers 17:3450-6.
Yinsong et al., 2007, Carbohydrate Polymers 69:597-606.
Zhao et al., 2009, Neurosci. 164:398-403.
U.S. Pat. No. 4,081,525.
U.S. Pat. No. 4,585,862.
U.S. patent application Ser. No. 12/806,950.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound having the structure

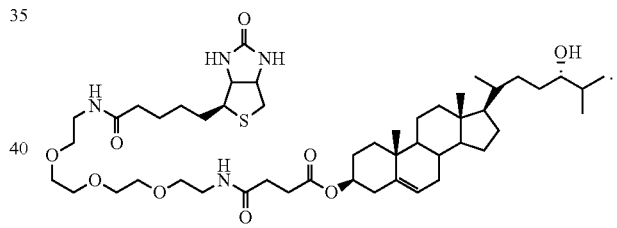

2. A compound having the structure

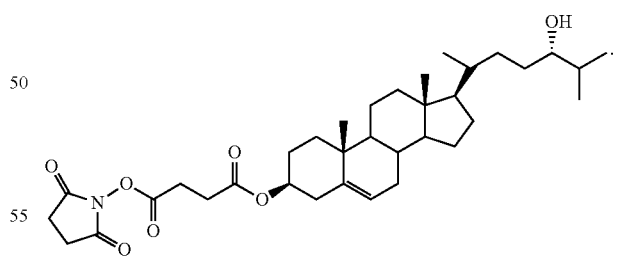

* * * * *

UNITED STATES PATENT AND TRADEMARK OFFICE
CERTIFICATE OF CORRECTION

PATENT NO.        : 10,197,583 B2                               Page 1 of 1
APPLICATION NO.   : 15/484754
DATED             : February 5, 2019
INVENTOR(S)       : Michael C. Mullenix et al.

It is certified that error appears in the above-identified patent and that said Letters Patent is hereby corrected as shown below:

Column 24, Line 35, Claim 1, the structure should show the stereo-conformation indicators for the two bonds in the cyclic amide (below HN and NH).

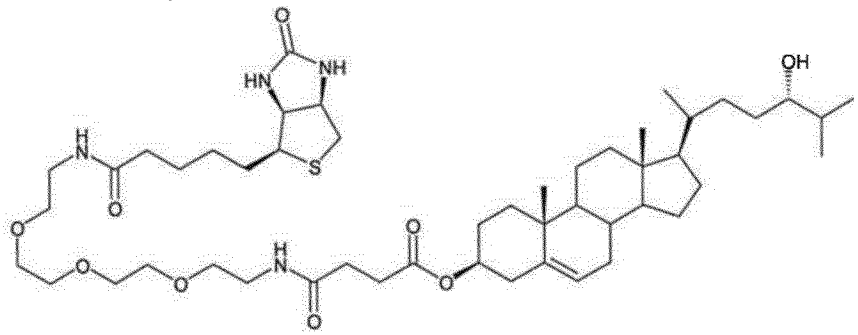

Signed and Sealed this
Sixth Day of August, 2019

Andrei Iancu
*Director of the United States Patent and Trademark Office*